United States Patent
Zhang

(10) Patent No.: US 9,115,165 B2
(45) Date of Patent: Aug. 25, 2015

(54) TETRACYCLIC ANTHRAQUINONE ANTIBIOTIC DERIVATIVES WITH HIGH ACTIVITY, PROCESS FOR PREPARING THE SAME AND USE THEREOF

(75) Inventor: Hesheng Zhang, Tianjin (CN)

(73) Assignees: Tianjin Hemay Bio-Tech Co., Ltd., Tianjin (CN); Tianjin Michele Sci-Tech Development Co., Ltd., Tianjin (CN)

( * ) Notice: Subject to any disclaimer, the term of this patent is extended or adjusted under 35 U.S.C. 154(b) by 383 days.

(21) Appl. No.: 12/937,367

(22) PCT Filed: Apr. 9, 2009

(86) PCT No.: PCT/CN2009/000385
§ 371 (c)(1),
(2), (4) Date: Jun. 1, 2011

(87) PCT Pub. No.: WO2009/124468
PCT Pub. Date: Oct. 15, 2009

(65) Prior Publication Data
US 2011/0224161 A1    Sep. 15, 2011

(30) Foreign Application Priority Data
Apr. 11, 2008 (CN) .......................... 2008 1 0052710

(51) Int. Cl.
*C07H 19/044* (2006.01)
*C07H 19/24* (2006.01)
*A61P 35/00* (2006.01)
*C07H 15/252* (2006.01)
*A61K 31/7056* (2006.01)
*A61K 31/7048* (2006.01)

(52) U.S. Cl.
CPC ............ *C07H 15/252* (2013.01); *C07H 19/044* (2013.01); *C07H 19/24* (2013.01)

(58) Field of Classification Search
CPC ..................................................... C07H 15/244
See application file for complete search history.

(56) References Cited

U.S. PATENT DOCUMENTS 5,304,687 A    4/1994    Bargiotti et al.

FOREIGN PATENT DOCUMENTS

| GB | 2 296 495 | 7/1996 | |
| WO | WO 97/19954 A1 * | 6/1997 | ............... C07K 7/23 |
| WO | WO 2004/082689 | 9/2004 | |

OTHER PUBLICATIONS

Morissette, S. L. et al., Advanced Drug Delivery Reviews, "High-throughput crystallization: polymorphs, salts, co-crystals and solvates of pharmaceutical solids", 2004, vol. 56, pp. 275-300.*
Vippagunta, S. R. et al., Advanced Drug Delivery Reviews, "Crystalline solids", 2001, vol. 48, pp. 3-26.*
International Search Report dated Jun. 17, 2009, issued in related International Application No. PCT/CN2009/000385, filed Apr. 9, 2009.

* cited by examiner

*Primary Examiner* — Shaojia Anna Jiang
*Assistant Examiner* — Bahar Craigo
(74) *Attorney, Agent, or Firm* — Kilpatrick Townsend & Stockton LLP

(57) ABSTRACT

The present invention relates to tetracyclic anthraquinone antibiotic derivatives with anticancer activity. The tetracyclic anthraquinone antibiotic derivatives as provided in the present invention have the same or higher activity than that of the known drugs such as doxorubicin, daunorubicin and the like in the cellular level while having better tolerance than that of doxorubicin and daunorubicin in the animal body.

12 Claims, No Drawings

TETRACYCLIC ANTHRAQUINONE ANTIBIOTIC DERIVATIVES WITH HIGH ACTIVITY, PROCESS FOR PREPARING THE SAME AND USE THEREOF

This application is a Continuation of International Application No. PCT/CN2009/000385, filed Apr. 9, 2009, which claims priority to Chinese Application No. 200810052710.3, filed Apr. 11, 2008, the contents of which are herein incorporated by reference in their entirety.

FIELD

The present invention relates to tetracyclic anthraquinone antibiotic derivatives with anticancer activity, process for preparing the same and use in the preparation of a medicament for treating tumor or cancer.

BACKGROUND

Tetracyclic anthraquinone antibiotics, in particular doxorubicin and daunorubicin, are widely used anticancer drugs. Doxorubicin has significant curative effects on a lot of solid tumors including liver cancer, gastric cancer, breast cancer, lung cancer, ovary cancer and multiple leukemias. Daunorubicin is one of the most effective drugs for treating leukemia. However, due to their side effects such as sever myelosuppression, cardiac toxicity, adverse reactions of digestive tracts and the like, their clinical applications are restricted. Up to now, a lot of derivatives of tetracyclic anthraquinones have already been separated from nature or prepared artificially. It is intended to find a new generation of anticancer drugs with high activity and low toxicity from these derivatives. The activity in the cellular level of doxorubicin derivative 2-pyrrolinyl-doxorubicin (AN-201) prepared by Attila A. Nagy, et al. is 300-1000 folds of doxorubicin. However, because of the high toxicity of AN-201, the anticancer activity was not observed at the maximal tolerance dose in the pathologic model of transplanted tumor in mice.

SUMMARY

The present invention relates to tetracyclic anthraquinone antibiotic derivatives with anticancer activity. The tetracyclic anthraquinone antibiotic derivatives as provided in the present invention have the same or higher activity than that of the known drugs such as doxorubicin, daunorubicin and the like in the cellular level while having better tolerance than that of doxorubicin and daunorubicin in the animal body.

Accordingly, the present invention relates to a compound represented by formula (I), and a salt or a solvate thereof:

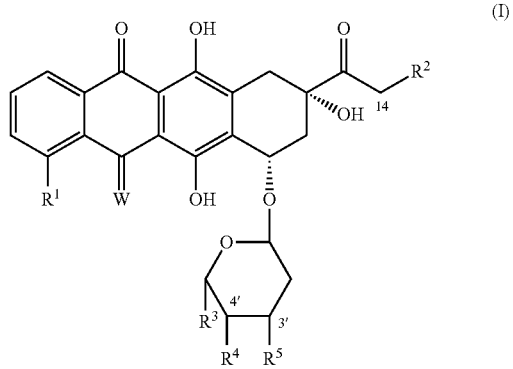

wherein $R^1$ represents H, $C_{1-4}$ hydrocarbyl or $OC_{1-4}$ hydrocarbyl;
$R^2$ represents H or $OR^6$, wherein, $R^6$ is selected from the group consisting of H, $C(O)R^8$, a peptide chain, $C(O)NH_2$, $C(O)NR^8R^9$, $C(O)Ar—R^{27}$, $C(O)(C_{2-4}$ hydrocarbylidene)COOH and a compound represented by formula (II); $R^8$ and $R^9$ each independently represent H or $C_{1-6}$ hydrocarbyl, or $NR^8R^9$ represents pyrrolidin-1-yl, piperidin-1-yl or morpholin-1-yl; Ar represents an aromatic ring or an aromatic heterocyclic ring; $R^{27}$ represents 0 to 5 identical or different groups selected from the group consisting of F, Cl, $NO_2$, CN, OH, SH, COOH, $NH_2$, $NR^8R^9$, $C_{1-6}$ hydrocarbyl, $OC_{1-6}$ hydrocarbyl, $OC(O)C_{1-6}$ hydrocarbyl, $C(O)OC_{1-6}$ hydrocarbyl, $SC_{1-6}$ hydrocarbyl, $S(O)C_{1-6}$ hydrocarbyl and $S(O)_2C_{1-6}$ hydrocarbyl; the peptide chain represents a single natural amino acid, a single unnatural amino acid or a peptide chain consisting of 2 to 4 natural amino acids and/or unnatural amino acids;

W represents O or NH;
$R^3$ represents H, F, $OC_{1-4}$ hydrocarbyl or $C_{1-4}$ hydrocarbyl;
$R^4$ represents H, F, $C_{1-4}$ hydrocarbyl or $OR^7$, wherein $R^7$ represents H, 2-pyranyl or $R^6$;
$R^5$ represents a compound represented by formula (III), a compound represented by formula (IV), a compound represented by formula (V) or maleimido,

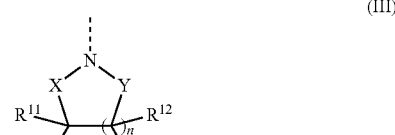

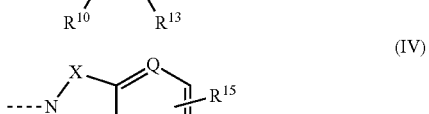

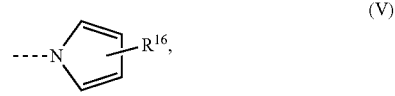

wherein
n represents 1 or 2;
X and Y each independently represent C=O or $CR^{21}R^{22}$;
Q represents CH or N;
$R^{10}$, $R^{11}$, $R^{12}$, $R^{13}$, $R^{15}$ and $R^{16}$ are each independently selected from the group consisting of H, F, Cl, CN, $NO_2$, $NH_2$, OH, $C(O)OC_{1-4}$ hydrocarbyl, $OC(O)C_{1-4}$ hydrocarbyl, $OC_{1-4}$ hydrocarbyl, $C_{1-4}$ hydrocarbyl, $SC_{1-6}$ hydrocarbyl, $S(O)C_{1-6}$ hydrocarbyl, $S(O)_2C_{1-6}$ hydrocarbyl, $(C_{0-4}$ hydrocarbylidene)Ar—$R^{27}$ and $NR^8R^9$; and
$R^{21}$ and $R^{22}$ each independently represent H or $C_{1-4}$ hydrocarbyl.

As used herein, $C_{1-4}$ hydrocarbyl may be a straight saturated or unsaturated hydrocarbyl or a branched saturated or unsaturated hydrocarbyl, and may be substituted with 0 to 4 identical or different substituents selected from the group consisting of F, Cl, CN, OH, $NO_2$, COOH, $C_{1-4}$ hydrocarbyl, NHC(O)$C_{1-6}$ hydrocarbyl, NHC(O)Ar—$R^{27}$ and $NR^8R^9$. $R^8$ and $R^9$ each independently represent H or $C_{1-6}$ hydrocarbyl, or $NR^8R^9$ is selected from the group consisting of pyrrolidin-1-yl, piperidin-1-yl and morpholin-1-yl.

As used herein, $C_{2-4}$ hydrocarbylidene may be a straight saturated or unsaturated hydrocarbylidene or a branched saturated or unsaturated hydrocarbylidene, and may be substituted with 0 to 3 identical or different substituents selected from the group consisting of F, Cl, CN, OH, $NO_2$, COOH, $C_{1-4}$ hydrocarbyl, NHC(O)$C_{1-6}$ hydrocarbyl, NHC(O)Ar—$R^{27}$ and $NR^8R^9$. $R^8$ and $R^9$ each independently represent H or $C_{1-6}$ hydrocarbyl, or $NR^8R^9$ is selected from the group consisting of pyrrolidin-1-yl, piperidin-1-yl and morpholin-1-yl.

As used herein, $C_{0-4}$ hydrocarbylidene may be a straight saturated or unsaturated hydrocarbylidene or a branched saturated or unsaturated hydrocarbylidene, and may be substituted with 0 to 3 identical or different substituents selected from the group consisting of F, Cl, CN, OH, $NO_2$, COOH, $C_{1-4}$ hydrocarbyl, NHC(O)$C_{1-6}$ hydrocarbyl, NHC(O)Ar—$R^{27}$ and $NR^8R^9$. $R^8$ and $R^9$ each independently represent H or $C_{1-6}$ hydrocarbyl, or $NR^8R^9$ is selected from the group consisting of pyrrolidin-1-yl, piperidin-1-yl and morpholin-1-yl.

As used herein, $C_{1-6}$ hydrocarbyl may be a straight saturated or unsaturated hydrocarbyl or a branched saturated or unsaturated hydrocarbyl, and may be substituted with 0 to 4 identical or different substituents selected from the group consisting of F, Cl, CN, OH, $NO_2$, COOH, $C_{1-4}$ hydrocarbyl, NHC(O)$C_{1-6}$ hydrocarbyl, NHC(O) Ar—$R^{27}$ and $NR^8R^9$. $R^8$ and $R^9$ each independently represent H or $C_{1-6}$ hydrocarbyl, or $NR^8R^9$ is selected from the group consisting of pyrrolidin-1-yl, piperidin-1-yl and morpholin-1-yl.

As used herein, an aromatic ring or an aromatic heterocyclic ring is selected from the group consisting of benzene, naphthalene, pyridine, pyrrole, thiophene, furan, pyrimidine and pyrazine.

A compound represented by formula (I), which is suitable to prepare a medicament for treating tumor or cancer, is a compound in which $R^1$ is selected from the group consisting of H, $CH_3$ and $OCH_3$. A compound of formula (I), which is the most suitable to prepare a medicament for treating tumor or cancer, is a compound in which $R^1$ represents H or $OCH_3$.

A compound represented by formula (I), which is suitable to prepare a medicament for treating tumor or cancer, is a compound in which $R^2$ represents H or $OR^6$, wherein $R^6$ is selected from the group consisting of H, glycyl, alanyl, valyl, leucinyl, isoleucinyl, phenylalanyl, serinyl, threonyl, tyrosinyl, lysinyl, 2-N,N-dimethylaminoacetyl, 2-N,N-diethylaminoacetyl, 2-piperidylacetyl, 2-morpholinylacetyl, 2,2-dimethylglycyl, 2,2-dimethyl-2-methylaminoacetyl, 2,2-dimethyl-2-(N,N-dimethylamino)acetyl, 2,2-dimethyl-2-ethylaminoacetyl, 2,2-dimethyl-2-(N,N-diethylamino)acetyl, 2,2-dimethyl-2-(N,N-dipropylamino)acetyl, 2,2-dimethyl-2-piperidylacetyl, 2,2-dimethyl-2-pyrrolinylacetyl, 2,2-dimethyl-2-morpholinylacetyl, 2,2-dimethyl-2-(N-methyl-N-ethylamino)acetyl, 2-phenylglycyl, 2-phenyl-2-methylaminoacetyl, 2-phenyl-2-(N,N-dimethylamino)acetyl, 2-phenyl-2-ethylaminoacetyl, 2-phenyl-2-(N,N-diethylamino)acetyl, 2-phenyl-2-(N,N-dipropylamino)acetyl, 2-phenyl-2-piperidylacetyl, 2-phenyl-2-pyrrolinylacetyl, 2-phenyl-2-morpholinylacetyl, 2-phenyl-2-(N-methyl-N-ethylamino)acetyl, acetyl, propionyl, butanoyl, pentanoyl, 3-methylaminopropionyl, 3-ethylaminopropionyl, 3-N,N-dimethylaminopropionyl, 3-N,N-diethylaminopropionyl, 3-piperidylpropionyl, 3-pyrrolidinylpropionyl, 3-morpholinylpropionyl, N-glycylglycyl, N-alanylglycyl, N-valylglycyl, N-serinylglycyl, N-glycylalanyl, N-alanylalanyl, N-valylalanyl, N-serinylalanyl, N-glycylvalyl, N-alanylvalyl, N-valylvalyl, N-serinylvalyl, hydrogen succinate group, (3-nitro-2-carboxyl)benzoate group, (2-carboxyl)benzoate group, (2,4-dicarboxyl)benzoate group, (3,4,5,6-tetrafluoro-2-carboxyl)benzoate group, (2-carboxyl-6-fluoro)benzoate group and (3-fluoro-2-carboxyl)benzoate group. A compound represented by formula (I), which is more suitable to prepare a medicament for treating tumor or cancer, is a compound in which $R^2$ represents H or $OR^6$, wherein $R^6$ is selected from the group consisting of H, glycyl, alanyl, valyl, leucinyl, isoleucinyl, phenylalanyl, serinyl, threonyl, tyrosinyl, lysinyl, 2-N,N-dimethylaminoacetyl, 2-N,N-diethylaminoacetyl, 2-piperidylacetyl, 2-morpholinylacetyl, 2,2-dimethylglycyl, 2-phenylglycyl, 3-methylaminopropionyl, 3-ethylaminopropionyl, hydrogen succinate group, (3-nitro-2-carboxyl)benzoate group, (2-carboxyl)benzoate group, (2,4-dicarboxyl)benzoate group, (3,4,5,6-tetrafluoro-2-carboxyl)benzoate group, (2-carboxyl-6-fluoro)benzoate group and (3-fluoro-2-carboxyl)benzoate group. A compound represented by formula (I), which is the most suitable to prepare a medicament for treating tumor or cancer, is a compound in which $R^2$ represents H or $OR^6$, wherein $R^6$ is selected from the group consisting of H, glycyl, alanyl, valyl, leucinyl, isoleucinyl, phenylalanyl, serinyl, threonyl, tyrosinyl, lysinyl, 2-N,N-dimethylaminoacetyl, 2-N,N-diethylaminoacetyl, 2-piperidylacetyl, 2-morpholinylacetyl, 2,2-dimethylglycyl, 2-phenylglycyl, hydrogen succinate group, (3-nitro-2-carboxyl)benzoate group, (2-carboxyl)benzoate group, (2,4-dicarboxyl)benzoate group, (3,4,5,6-tetrafluoro-2-carboxyl)benzoate group, (2-carboxyl-6-fluoro)benzoate group and (3-fluoro-2-carboxyl)benzoate group.

A compound represented by formula (I), which is suitable to prepare a medicament for treating tumor or cancer, is a compound in which W represents O or NH. A compound represented by formula (I), which is the most suitable to prepare a medicament for treating tumor or cancer, is a compound in which W represents O.

A compound represented by formula (I), which is suitable to prepare a medicament for treating tumor or cancer, is a compound in which $R^3$ is selected from the group consisting of H, F, $CH_3$, $CH_2CH_3$, $OCH_3$ and $OCH_2CH_3$. A compound represented by formula (I), which is more suitable to prepare a medicament for treating tumor or cancer, is a compound in which $R^3$ is selected from the group consisting of H, $CH_3$ and $OCH_3$. A compound represented by formula (I), which is the most suitable to prepare a medicament for treating tumor or cancer, is a compound in which $R^3$ represents $CH_3$.

A compound represented by formula (I), which is suitable to prepare a medicament for treating tumor or cancer, is a compound in which $R^4$ is selected from the group consisting of H, F, OH, $CH_3$, $OCH_3$, 2-pyranyl, hydrogen succinate group, (3-nitro-2-carboxyl)benzoate group, (2-carboxyl)benzoate group, (2,4-dicarboxyl)benzoate group, (3,4,5,6-tetrafluoro-2-carboxyl)benzoate group, (2-carboxyl-6-fluoro)benzoate group and (3-fluoro-2-carboxyl)benzoate group. A compound represented by formula (I), which is more suitable to prepare a medicament for treating tumor or cancer, is a compound in which $R^4$ is selected from the group consisting of OH, $OCH_3$, 2-pyranyl and hydrogen succinate group. A compound represented by formula (I), which is the most suitable to prepare a medicament for treating tumor or cancer, is a compound in which $R^4$ is selected from the group consisting of OH, 2-pyranyl and hydrogen succinate group.

A compound represented by formula (I), which is suitable to prepare a medicament for treating tumor or cancer, is a compound in which $R^5$ is selected from the group consisting of pyrrol-1-yl, succinimido, glutarimido, butyrolactam-1-yl, valerolactam-1-yl, 3-methyl-pyrrol-1-yl, 3-methoxy-pyrrol- 1-yl, 3-methyl-succinimido, 3-methoxy-succinimido, 3-methyl-glutarimido, 3-methoxy-glutarimido, 3-methyl-butyrolactam-1-yl, 3-methoxy-butyrolactam-1-yl, 3-methyl-valerolactam-1-yl, 3-methoxy-valerolactam-1-yl, 4-methyl-valerolactam-1-yl, 4-methoxy-valerolactam-1-yl, benzosuccinimido-1-yl and pyridosuccinimido-1-yl. A compound represented by formula (I), which is the most suitable to prepare a medicament for treating tumor or cancer, is a compound in which $R^5$ is selected from the group consisting of pyrrol-1-yl, succinimido, glutarimido, butyrolactam-1-yl and valerolactam-1-yl.

In the present invention, a compound which has a chiral centre and is not specifically identified as R or S configuration in the structural formula in the Specification and Claims may be a compound of R configuration, a compound of S configuration, or a mixture thereof.

The scope of protection in the present invention should also include a prodrug, a salt or an active metabolite of the compound disclosed in the present invention.

The present invention discloses several processes for preparing a compound represented by formula (VI), which is an important intermediate of a compound represented by formula (I).

Process 1:

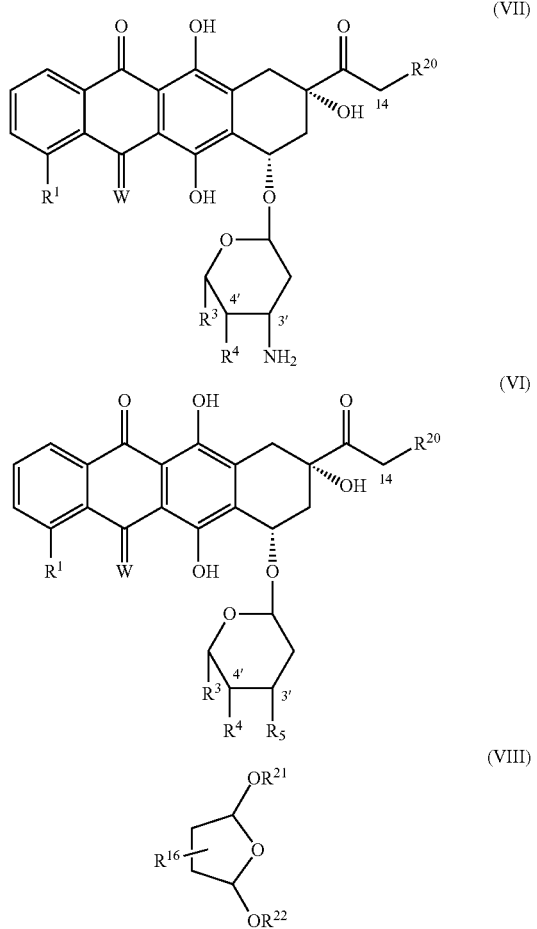

Groups represented by $R^1$, $R^3$, $R^4$ and W in a compound represented by formula (VII) are the same as the groups represented by $R^1$, $R^3$, $R^4$ and W in a compound represented by formula (I). $R^{20}$ represents H or OH. Groups represented by $R^1$, $R^3$, $R^4$, $R^5$ and W in a compound represented by formula (VI) are the same as the groups represented by $R^1$, $R^3$, $R^4$, $R^5$ and W in a compound represented by formula (I). $R^{20}$ represents H or OH. A group represented by $R^{16}$ in a compound represented by formula (VIII) is the same as the group represented by $R^{16}$ in a compound represented by formula (V). $R^{21}$ and $R^{22}$ each independently represent H or $C_{1-4}$ hydrocarbyl.

As described herein, a salt of a compound represented by formula (VII) is a salt of a compound represented by formula (VII) reacting with an acid which is selected from the group consisting of hydrochloric acid, sulfuric acid, phosphoric acid, formic acid, acetic acid, methylsulfonic acid, benzene sulfonic acid, p-toluene sulfonic acid and a mixture thereof.

A compound represented by formula (VI) is obtained by reacting a compound represented by formula (VII) or a salt thereof with a compound represented by formula (VIII) in the presence of an acidic and/or basic reagent, in which the acidic reagent is selected from the group consisting of hydrochloric acid, sulfuric acid, phosphoric acid, formic acid, acetic acid, propionic acid, butyric acid, pentanoic acid, hexanoic acid, methylsulfonic acid, benzene sulfonic acid, p-toluene sulfonic acid, citric acid, tartaric acid, lactic acid, malic acid and a mixture thereof. The amount of the acidic reagent is 0.05 to 500 folds (moles) of a compound represented by formula (VII). More suitable amount of the acidic reagent is 0.2 to 50 folds (moles) of a compound represented by formula (VII). The most suitable amount of the acidic reagent is 0.7 to 5 folds (moles) of a compound represented by formula (VII). The basic reagent is selected from the group consisting of potassium carbonate, cesium carbonate, sodium carbonate, sodium bicarbonate, potassium bicarbonate, sodium hydroxide, potassium hydroxide, sodium acetate, potassium acetate, sodium phosphate, potassium phosphate, disodium hydrogen phosphate, dipotassium hydrogen phosphate, sodium lactate, potassium lactate, sodium citrate, potassium citrate, sodium tartrate, potassium tartrate, sodium malate, potassium malate, sodium propionate, potassium propionate, sodium butyrate, potassium butyrate, sodium succinate, potassium succinate, sodium valerate, potassium valerate, sodium glutarate, potassium glutarate, triethylamine, trimethylamine, diisopropylethylamine, 4-dimethylamino pyridine, 4-(pyrrolidin-1-yl)pyridine, pyridine, N-methylmorpholine and a mixture thereof. The amount of the basic reagent is 0.05 to 500 folds (moles) of a compound represented by formula (VII). More suitable amount of the basic reagent is 0.2 to 50 folds (moles) of a compound represented by formula (VII). The most suitable amount of the basic reagent is 0.7 to 5 folds (moles) of a compound represented by formula (VII). The reaction temperature is −20 to 150° C. More suitable reaction temperature is −10 to 100° C. The most suitable reaction temperature is −10 to 80° C. The reaction is carried out in a solvent such as dichloromethane, chloroform, N,N-dimethylformamide, dimethyl sulfoxide, ethylene glycol dimethyl ether, ethylene glycol monomethyl ether, ethanol, methanol, isopropanol, tetrahydrofuran, ethyl acetate, methyl acetate, methyl propionate, ethyl propionate, ethylene glycol diethyl ether, ethylene glycol monoethyl ether, N,N-diethylformamide, 1,2-dichloroethane, acetonitrile, water, a compound represented by formula (VIII) or a mixture thereof. If necessary, an organic base such as triethylamine, trimethylamine, diisopropylethylamine, 4-dimethylamino pyridine, 4-(pyrrolidin-1-yl)pyridine, pyridine, N-methylmorpholine and the like can be used as a catalyst in the reaction. Where an organic base is used as a catalyst, the molar amount of the organic base is 0.01 to 2 folds of a compound represented by formula (VII). More suitable molar amount of the organic base is 0.05 to 0.2 folds of a compound represented by formula (VII). The feed ratio by mole of a compound represented by formula (VII) or a salt thereof to a compound represented by formula (VIII) is 1:0.1 to 1:10000. More suitable feed ratio by mole of a compound represented by formula (VII) or a salt thereof to a compound represented by formula (VIII) is 1:0.5 to 1:1000. The most suitable feed ratio by mole of a compound represented by formula (VII) or a salt thereof to a compound represented by formula (VIII) is 1:1 to 1:500.

The second process for preparing a compound represented by formula (VI) disclosed in the present invention:

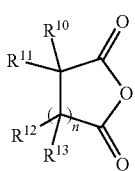

(IX)

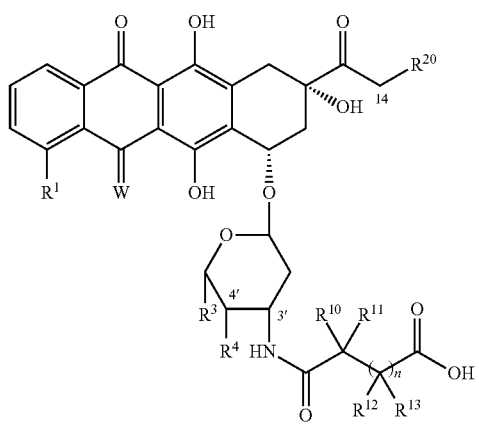

(X)

wherein groups represented by $R^{10}$, $R^{11}$, $R^{12}$, $R^{13}$ and n in a compound represented by formula (IX) are the same as the groups represented by $R^{10}$, $R^{11}$, $R^{12}$, $R^{13}$ and n in a compound represented by formula (III); groups represented by $R^{10}$, $R^{11}$, $R^{12}$, $R^{13}$ and n in a compound represented by formula (X) are the same as the groups represented by $R^{10}$, $R^{11}$, $R^{12}$, $R^{13}$ and n in a compound represented by formula (III); groups represented by $R^1$, $R^3$, $R^4$ and W in a compound represented by formula (X) are the same as the groups represented by $R^1$, $R^3$, $R^4$ and W in a compound represented by formula (VII); $R^{20}$ represents H or OH.

A compound represented by formula (X) is obtained by reacting a compound represented by formula (VII) or a salt thereof with a compound represented by formula (IX). The reaction is carried out in a solvent such as dichloromethane, chloroform, carbon tetrachloride, ethyl acetate, methyl acetate, methyl propionate, ethyl propionate, 1,2-dichloroethane, acetone, tetrahydrofuran, ethylene glycol dimethyl ether, ethylene glycol diethyl ether, N,N-dimethylformamide, N,N-diethylformamide, dimethyl sulfoxide, acetonitrile, water or a mixture thereof. Pyridine, 4-dimethylamino pyridine, 4-diethylamino pyridine, 4-(pyrrolidin-1-yl)pyridine or a mixture thereof can be optionally added as a catalyst in the reaction. The molar amount of the catalyst is 0.01 to 10 folds of a compound represented by formula (VII). More suitable molar amount of the catalyst is 0.02 to 5 folds of a compound represented by formula (VII). The optimal molar amount of the catalyst is 0.05 to 1 fold of a compound represented by formula (VII). Triethylamine, trimethylamine, pyridine, diisopropylethylamine, N-methylmorpholine, N-methyl piperidine, N-ethyl piperidine, 4-dimethylamino pyridine, 4-diethylamino pyridine, 4-(pyrrolidin-1-yl)pyridine, potassium carbonate, sodium carbonate, sodium bicarbonate, potassium bicarbonate, cesium carbonate, sodium hydroxide, potassium hydroxide or a mixture thereof can be added as an acid binding agent in the reaction. The molar amount of the acid binding agent is 0.4 to 20 folds of a compound represented by formula (VII). More suitable molar amount of the acid binding agent is 0.8 to 10 folds of a compound represented by formula (VII). The optimal molar amount of the acid binding agent is 1 to 5 folds of a compound represented by formula (VII). The reaction temperature is −20 to 100° C. More suitable temperature is −10 to 80° C. The optimal reaction temperature is −5 to 80° C. The feed ratio by mole of a compound represented by formula (IX) to a compound represented by formula (VII) or a salt thereof is 1:0.1 to 1:10. The more suitable feed ratio by mole of a compound represented by formula (IX) to a compound represented by formula (VII) or a salt thereof is 1:0.5 to 1:5. The most suitable feed ratio by mole of a compound represented by formula (IX) to a compound represented by formula (VII) or a salt thereof is 1:0.8 to 1:3.

A compound represented by formula (VI) is obtained with a compound represented by formula (X) in the presence of a dehydrating agent. The dehydrating agent is selected from the group consisting of DCC (dicyclohexyl carbodiimide), EDC HCl (1-ethyl-3-(3-dimethylamino propyl) carbodiimide hydrochloride), CDI (N,N'-carbonyldiimidazole) and DIC (N,N'-diisopropyl carbodiimide). The molar amount of the dehydrating agent is 0.1 to 10 folds of a compound represented by formula (X). More suitable molar amount of the dehydrating agent is 0.5 to 5 folds of a compound represented by formula (X). The optimal molar amount of the dehydrating agent is 1 to 3 folds of a compound represented by formula (X). The reaction temperature is −10 to 120° C. More suitable temperature is 0 to 100° C. The most suitable reaction temperature is 0 to 80° C. The reaction is carried out in a solvent such as dichloromethane, chloroform, ethyl acetate, methyl acetate, ethyl propionate, methyl propionate, acetone, tetrahydrofuran, ethylene glycol dimethyl ether, ethylene glycol diethyl ether, N,N-dimethylformamide, N,N-diethylformamide, dimethyl sulfoxide or acetonitrile or a mixture thereof.

The third process for preparing a compound represented by formula (VI) disclosed in the present invention:

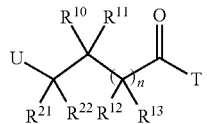

(XI)

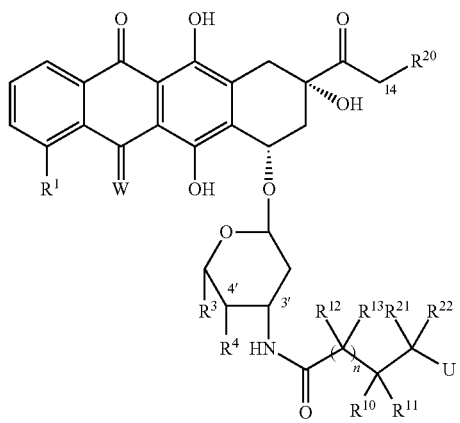

(XIII)

wherein groups represented by $R^{10}$, $R^{11}$, $R^{12}$, $R^{13}$, $R^{21}$, $R^{22}$ and n in a compound represented by formula (XI) are the same as the groups represented by $R^{10}$, $R^{11}$, $R^{12}$, $R^{13}$, $R^{21}$, $R^{22}$ and n in a compound represented by formula (III); U is selected from the group consisting of Cl, Br, I, OTs (p-toluenesulfonate group) and OMs (methanesulfonate group); T is selected from the group consisting of F, Cl, Br, OSu, OBt and OAt. Groups represented by $R^{10}$, $R^{11}$, $R^{12}$, $R^{13}$, $R^{21}$, $R^{22}$, n and U in a compound represented by formula (XIII) are the same as the groups represented by $R^{10}$, $R^{11}$, $R^{12}$, $R^{13}$, $R^{21}$, $R^{22}$, n and U in a compound represented by formula (XI). Groups represented by $R^1$, $R^3$, $R^4$, $R^{20}$ and W in a compound represented by formula (X) are the same as the groups represented by $R^1$, $R^3$, $R^4$, $R^{20}$ and W in a compound represented by formula (VII).

A compound represented by formula (XIII) is obtained by reacting a compound represented by formula (VII) or a salt thereof with a compound represented by formula (XI) in the presence of a base. The base is selected from the group consisting of triethylamine, trimethylamine, diisopropylethylamine, pyridine, 4-dimethylamino pyridine, 4-diethylamino pyridine, 4-(pyrrolidin-1-yl)pyridine, N-methylmorpholine, N-methyl piperidine, N-ethyl piperidine, cesium carbonate, potassium carbonate, sodium carbonate, sodium bicarbonate, potassium bicarbonate, sodium hydroxide, potassium hydroxide and a mixture thereof. The molar amount of the base is 0.5 to 10 folds of a compound represented by formula (VII) or a salt thereof. More suitable molar amount of the base is 0.8 to 7 folds of a compound represented by formula (VII) or a salt thereof. The most suitable molar amount of the base is 1 to 5 folds of a compound represented by formula (VII) or a salt thereof. The reaction is carried out in a solvent such as dichloromethane, chloroform, 1,2-dichloroethane, acetone, ethyl acetate, isopropanol, methyl acetate, propyl acetate, methyl propionate, ethyl propionate, acetonitrile, ethanol, N,N-dimethylformamide, N,N-diethylformamide, dimethyl sulfoxide, tetrahydrofuran, ethylene glycol dimethyl ether, ethylene glycol diethyl ether, ethylene glycol monomethyl ether, ethylene glycol monoethyl ether, ethylene glycol, ethanol, propanol, water or a mixture thereof. The reaction temperature is −20 to 120° C. More suitable temperature is −10 to 100° C. The most suitable reaction temperature is 0 to 80° C. The feed ratio by mole of a compound represented by formula (VII) or a salt thereof to a compound represented by formula (XI) is 1:0.2 to 1:10. More suitable feed ratio by mole of a compound represented by formula (VII) or a salt thereof to a compound represented by formula (XI) is 1:0.5 to 1:5. The optimal feed ratio by mole of a compound represented by formula (VII) or a salt thereof to a compound represented by formula (XI) is 1:0.8 to 1:3.

A compound represented by formula (VI) is obtained by a compound represented by formula (XIII) in the presence of a basic reagent. The basic reagent is selected from the group consisting of triethylamine, trimethylamine, diisopropylethylamine, pyridine, 4-dimethylamino pyridine, 4-diethylamino pyridine, 4-(pyrrolidin-1-yl)pyridine, N-methylmorpholine, N-methyl piperidine, N-ethyl piperidine, cesium carbonate, potassium carbonate, sodium carbonate, sodium bicarbonate, potassium bicarbonate, sodium hydroxide, potassium hydroxide, sodium hydride, potassium hydride, lithium hexamethyldisilazide, potassium hexamethyldisilazide, sodium hexamethyldisilazide and a mixture thereof. The molar amount of the basic reagent is 0.5 to 3 folds of a compound represented by formula (XIII) or a salt thereof. More suitable molar amount of the basic reagent is 0.8 to 2 folds of a compound represented by formula (XIII) or a salt thereof. The most suitable molar amount of the basic reagent is 1 to 1.5 folds of a compound represented by formula (XIII) or a salt thereof. The reaction is carried out in a solvent such as dichloromethane, chloroform, 1,2-dichloroethane, acetone, ethyl acetate, isopropanol, methyl acetate, propyl acetate, methyl propionate, ethyl propionate, acetonitrile, ethanol, N,N-dimethylformamide, N,N-diethylformamide, dimethyl sulfoxide, tetrahydrofuran, ethylene glycol dimethyl ether, ethylene glycol diethyl ether or a mixture thereof. The reaction temperature is −20 to 120° C. More suitable temperature is −10 to 100° C. The most suitable reaction temperature is 0 to 80° C.

The fourth process for preparing a compound represented by formula (VI) disclosed in the present invention:

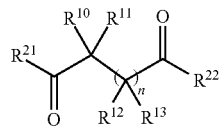

(XIV)

Groups represented by $R^{10}$, $R^{11}$, $R^{12}$, $R^{13}$, $R^{21}$, $R^{22}$ and n in a compound represented by formula (XIV) are the same as the groups represented by $R^{10}$, $R^{11}$, $R^{12}$, $R^{13}$, $R^{21}$, $R^{22}$ and n in a compound represented by formula (III).

A compound represented by formula (VI) is obtained by reacting a compound represented by formula (XIV) or a salt thereof with a compound represented by formula (VII) in the presence of an acidic and/or basic reagent, in which the basic reagent is selected from the group consisting of trimethylamine, triethylamine, pyridine, N-methylmorpholine, N-methyl piperidine, N-ethyl piperidine, diisopropylethylamine, potassium carbonate, sodium carbonate, cesium carbonate, sodium bicarbonate, potassium bicarbonate and a mixture thereof. The molar amount of the basic reagent is 0.5 to 10 folds of a compound represented by formula (VII) or a salt thereof. More suitable molar amount of the basic reagent is 0.8 to 5 folds of a compound represented by formula (VII) or a salt thereof. The most suitable molar amount of the basic reagent is 1 to 3 folds of a compound represented by formula (VII) or a salt thereof. The acidic reagent is selected from the group consisting of hydrochloric acid, sulfuric acid, phosphoric acid, formic acid, acetic acid, propionic acid, butyric acid, pentanoic acid, hexanoic acid, methylsulfonic acid, benzene sulfonic acid, p-toluene sulfonic acid, citric acid, tartaric acid, lactic acid, malic acid and a mixture thereof. The amount of the acidic reagent is 0.05 to 500 folds (moles) of a compound represented by formula (VII). More suitable amount of the acidic reagent is 0.2 to 50 folds (moles) of a compound represented by formula (VII). The most suitable amount (moles) of the acidic reagent is 0.7 to 5 folds (moles) of a compound represented by formula (VII). The reaction is carried out in a solvent such as dichloromethane, chloroform, acetone, acetonitrile, ethyl acetate, methanol, ethanol, propanol, isopropanol, butanol, ethylene glycol, tetrahydrofuran, ethylene glycol dimethyl ether, ethylene glycol diethyl ether, ethylene glycol monomethyl ether, ethylene glycol monoethyl ether, methyl acetate, propyl acetate, methyl propionate, ethyl propionate, N,N-dimethylformamide, N,N-diethylformamide, dimethyl sulfoxide or a mixture thereof. The reaction temperature is −20 to 100° C. More suitable temperature is −10 to 80° C. The most suitable reaction temperature is 0 to 50° C.

The fifth process for preparing a compound represented by formula (VI) disclosed in the present invention:

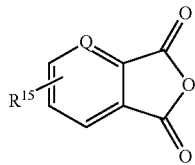
(XV)

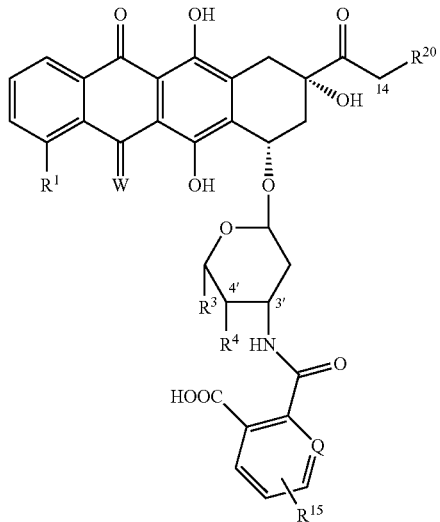
(XVI)

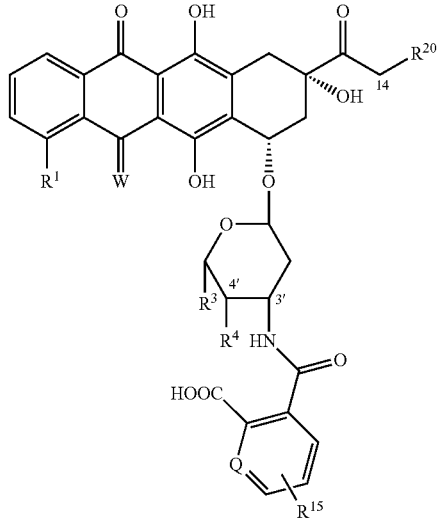
(XVII)

wherein groups represented by $R^{15}$ and Q in the formula (XV) are the same as the groups represented by $R^{15}$ and Q in formula (IV). Groups represented by $R^{15}$ and Q in the formula (XVI) are the same as the groups represented by $R^{15}$ and Q in formula (IV). Groups represented by $R^1$, $R^3$, $R^4$, $R^{20}$ and W in the formula (XVI) are the same as the groups represented by $R^1$, $R^3$, $R^4$, $R^{20}$ and W in a compound represented by formula (VII). Groups represented by $R^{15}$ and Q in the formula (XVII) are the same as the groups represented by $R^{15}$ and Q in formula (IV). Groups represented by $R^1$, $R^3$, $R^4$, $R^{20}$ and W in the formula (XVII) are the same as the groups represented by $R^1$, $R^3$, $R^4$, $R^{20}$ and W in a compound represented by formula (VII).

A compound represented by formula (XVI) or formula (XVII) is obtained by reacting a compound represented by formula (VII) or a salt thereof with a compound represented by formula (XV). The reaction is carried out in a solvent such as dichloromethane, chloroform, carbon tetrachloride, ethyl acetate, methyl acetate, methyl propionate, ethyl propionate, 1,2-dichloroethane, acetone, tetrahydrofuran, ethylene glycol dimethyl ether, ethylene glycol diethyl ether, N,N-dimethylformamide, N,N-diethylformamide, dimethyl sulfoxide, acetonitrile, water or a mixture thereof. Pyridine, 4-dimethylamino pyridine, 4-diethylamino pyridine, 4-(pyrrolidin-1-yl)pyridine or a mixture thereof can be optionally added as a catalyst in the reaction. The molar amount of the catalyst is 0.01 to 10 folds of a compound represented by formula (VII). More suitable molar amount of the catalyst is 0.02 to 5 folds of a compound represented by formula (VII). The optimal molar amount of the catalyst is 0.05 to 1 fold of a compound represented by formula (VII). Triethylamine, trimethylamine, pyridine, diisopropylethylamine, N-methylmorpholine, N-methyl piperidine, N-ethyl piperidine, 4-dimethylamino pyridine, 4-diethylamino pyridine, 4-(pyrrolidin-1-yl)pyridine, potassium carbonate, sodium carbonate, sodium bicarbonate, potassium bicarbonate, cesium carbonate, sodium hydroxide, potassium hydroxide or a mixture thereof can be optionally added as an acid binding agent in the reaction. The molar amount of the acid binding agent is 0.4 to 20 folds of a compound represented by formula (VII). More suitable molar amount of the acid binding agent is 0.8 to 10 folds of a compound represented by formula (VII). The optimal molar amount of the acid binding agent is 1 to 5 folds of a compound represented by formula (VII). The reaction temperature is −20 to 100° C. More suitable temperature is −10 to 80° C. The most suitable reaction temperature is 0 to 80° C. The feed ratio by mole of a compound represented by formula (VII) or a salt thereof to a compound represented by formula (XV) is 1:0.2 to 1:10. More suitable feed ratio by mole of a compound represented by formula (VII) or a salt thereof to a compound represented by formula (XV) is 1:0.5 to 1:5. The most suitable feed ratio by mole of a compound represented by formula (VII) or a salt thereof to a compound represented by formula (XV) is 1:0.8 to 1:3.

A compound represented by formula (VI) can be obtained with a compound represented by formula (XVI) or formula (XVII) in the presence of a dehydrating agent. The dehydrating agent is selected from the group consisting of DCC (dicyclohexyl carbodiimide), EDC HCl (1-ethyl-3-(3-dimethylamino propyl) carbodiimide hydrochloride), CDI (N,N'-carbonyldiimidazole) and DIC(N,N'-diisopropyl carbodiimide). The molar amount of the dehydrating agent is 0.1 to 10 folds of a compound represented by formula (XVI) or (XVII). More suitable molar amount of the dehydrating agent is 0.5 to 5 folds of a compound represented by formula (XVI) or (XVII). The optimal molar amount of the dehydrating agent is 1 to 3 folds of a compound represented by formula (XVI) or (XVII). The reaction temperature is −10 to 120° C. More suitable temperature is 0 to 100° C. The most suitable reaction temperature is 20 to 100° C. The reaction is carried out in a solvent such as dichloromethane, chloroform, ethyl acetate, methyl acetate, ethyl propionate, methyl propionate, acetone, tetrahydrofuran, ethylene glycol dimethyl ether, ethylene glycol diethyl ether, N,N-dimethylformamide, N,N-diethylformamide, dimethyl sulfoxide, acetonitrile or a mixture thereof. Pyridine, 4-dimethylamino pyridine, 4-diethylamino pyridine, 4-(pyrrolidin-1-yl)pyridine or a mixture thereof can be added as a catalyst in the reaction. The molar amount of the catalyst is 0.01 to 1 fold of a compound represented by formula (XVI) or (XVII). More suitable molar amount of the catalyst is 0.02 to 0.8 folds of a compound represented by formula (XVI) or (XVII). The optimal molar amount of the catalyst is 0.03 to 0.5 folds of a compound represented by formula (XVI) or (XVII).

The sixth process for preparing a compound represented by formula (VI) disclosed in the present invention:

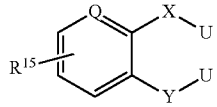

(XX)

Groups represented by $R^{15}$, X, Y and Q in a compound represented by formula (XX) are the same as the groups represented by $R^{15}$, X, Y and Q in a compound represented by formula (IV). U in a compound represented by formula (XX) represents Cl, Br, OMs (methanesulfonate group) or OTs (p-toluenesulfonate group).

A compound represented by formula (VI) can be obtained by reacting a compound represented by formula (VII) or a salt thereof with a compound represented by formula (XX) in the presence of a base. The reaction is carried out in a solvent such as dichloromethane, chloroform, carbon tetrachloride, ethyl acetate, methyl acetate, methyl propionate, ethyl propionate, 1,2-dichloroethane, acetone, tetrahydrofuran, ethylene glycol dimethyl ether, ethylene glycol diethyl ether, N,N-dimethylformamide, N,N-diethylformamide, dimethyl sulfoxide, acetonitrile, water or a mixture thereof. Pyridine, 4-dimethylamino pyridine, 4-diethylamino pyridine, 4-(pyrrolidin-1-yl)pyridine or a mixture thereof can be optionally added as a catalyst in the reaction. The molar amount of the catalyst is 0.01 to 10 folds of a compound represented by formula (VII). More suitable molar amount of the catalyst is 0.02 to 5 folds of a compound represented by formula (VII). The optimal molar amount of the catalyst is 0.05 to 1 fold of a compound represented by formula (VII). A base which can be added in the reaction includes, but is not limited to, triethylamine, trimethylamine, pyridine, diisopropylethylamine, N-methylmorpholine, N-methyl piperidine, N-ethyl piperidine, 4-dimethylamino pyridine, 4-diethylamino pyridine, 4-(pyrrolidin-1-yl)pyridine, potassium carbonate, sodium carbonate, sodium bicarbonate, potassium bicarbonate, cesium carbonate, sodium hydroxide, potassium hydroxide or a mixture thereof. The molar amount of the base to be added in the reaction is 0.4 to 20 folds of a compound represented by formula (VII). More suitable molar amount of the base to be added in the reaction is 0.8 to 10 folds of a compound represented by formula (VII). The optimal molar amount of the base to be added in the reaction is 1 to 5 folds of a compound represented by formula (VII). The reaction temperature is −20 to 100° C. More suitable temperature is −10 to 80° C. The optimal reaction temperature is 0 to 80° C. The feed ratio by mole of a compound represented by formula (VII) or a salt thereof to a compound represented by formula (XX) is 1:0.2 to 1:10. More suitable feed ratio by mole of a compound represented by formula (VII) or a salt thereof to a compound represented by formula (XX) is 1:0.5 to 1:5. The most suitable feed ratio by mole of a compound represented by formula (VII) or a salt thereof to a compound represented by formula (XX) is 1:0.8 to 1:3.

The first process for preparing a compound represented by formula (I) disclosed in the present invention:

A compound represented by formula (I) is obtained by reacting a compound represented by formula (VI) in which $R^{20}$ represents OH with $R^8COOH$, a peptide chain, HOOC—Ar—$R^{27}$, a compound represented by formula (IX), a compound represented by formula (XV) or a compound represented by formula (XXI)

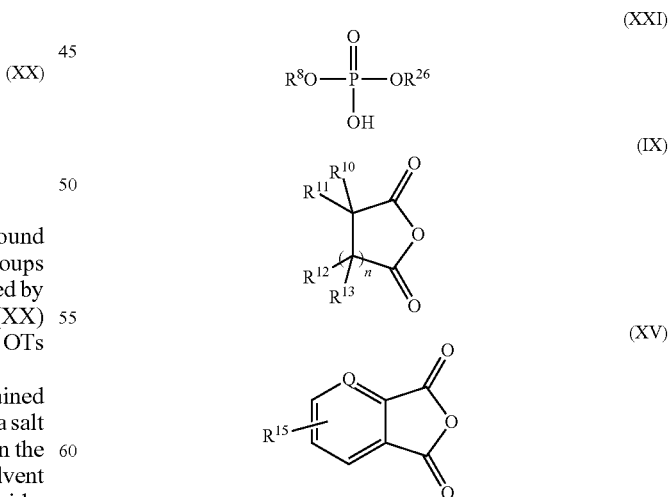

wherein $R^8$ in $R^8COOH$ represents H or $C_{1-6}$ hydrocarbyl; $R^8$ and $R^{26}$ in a compound represented by formula (XXI) each independently represent H or $C_{1-6}$ hydrocarbyl; Ar represents an aromatic ring or an aromatic heterocyclic ring; $R^{27}$ represents 0 to 5 identical or different groups selected from the group consisting of F, Cl, $NO_2$, CN, OH, SH, COOH, $NH_2$, $NR^8R^9$, $C_{1-6}$ hydrocarbyl, $OC_{1-6}$ hydrocarbyl, $OC(O)C_{1-6}$ hydrocarbyl, $C(O)OC_{1-6}$ hydrocarbyl, $SC_{1-6}$ hydrocarbyl, $S(O)C_{1-6}$ hydrocarbyl and $S(O)_2C_{1-6}$ hydrocarbyl. A peptide chain has free carboxyl and the N-terminal has 0 to 2 identical or different $C_{1-6}$ hydrocarbyl groups or has an amino protecting group, in which the amino protecting group is selected from the group consisting of Fmoc, Boc, CBZ, Tr and Alloc.

A condensation agent can be added in the reaction. The condensation agent is selected from the group consisting of DCC, EDC HCl, CDI, DIC and a mixture thereof. The molar amount of the condensation agent is 0.1-10 folds of a compound represented by formula (VI). More suitable molar amount of the condensation agent is 0.5 to 5 folds of a compound represented by formula (VI). The optimal molar amount of the condensation agent is 1 to 3 folds of a compound represented by formula (VI). The reaction temperature is −10 to 120° C. More suitable temperature is 0 to 100° C. The optimal reaction temperature is 20 to 100° C. The reaction is carried out in a solvent such as dichloromethane, chloroform, ethyl acetate, methyl acetate, ethyl propionate, methyl propionate, acetone, tetrahydrofuran, ethylene glycol dimethyl ether, ethylene glycol diethyl ether, N,N-dimethylformamide, N,N-diethylformamide, dimethyl sulfoxide, acetonitrile or a mixture thereof. Pyridine, 4-dimethylamino pyridine, 4-diethylamino pyridine, 4-(pyrrolidin-1-yl)pyridine or a mixture thereof can be optionally added as a catalyst in the reaction. The molar amount of the catalyst is 0.01 to 10 folds of a compound represented by formula (VI). More suitable molar amount of the catalyst is 0.02 to 5 folds of a compound represented by formula (VI). The optimal molar amount of the catalyst is 0.05 to 1 fold of a compound represented by formula (VI). The feed ratio by mole of a compound represented by formula (VI) to $R^8COOH$, a peptide chain, $HOOC—Ar—R^{27}$ or a compound represented by formula (XXI) is 1:0.2 to 1:10. More suitable feed ratio by mole of a compound represented by formula (VI) to $R^8COOH$, a peptide chain, $HOOC—Ar—R^{27}$ or a compound represented by formula (XXI) is 1:0.5 to 1:7. The optimal feed ratio by mole of a compound represented by formula (VI) to $R^8COOH$, a peptide chain, $HOOC—Ar—R^{27}$ or a compound represented by formula (XXI) is 1:0.8 to 1:5. If necessary, a base can be added as an acid binding agent in the reaction. The base which can be added in the reaction includes, but is not limited to, triethylamine, trimethylamine, pyridine, diisopropylethylamine, N-methylmorpholine, N-methyl piperidine, N-ethyl piperidine, 4-dimethylamino pyridine, 4-diethylamino pyridine, 4-(pyrrolidin-1-yl)pyridine, potassium carbonate, sodium carbonate, sodium bicarbonate, potassium bicarbonate, cesium carbonate, sodium hydroxide, potassium hydroxide or a mixture thereof. The molar amount of the base to be added in the reaction is 0.4 to 20 folds of a compound represented by formula (VI). More suitable molar amount of the base to be added in the reaction is 0.8 to 10 folds of a compound represented by formula (VI). The optimal molar amount of the base to be added in the reaction is 1 to 5 folds of a compound represented by formula (VI).

Through a conventional deprotection reaction used by a person skilled in the art, the object compound is prepared from a product which is obtained by reacting a compound represented by formula (VI) with a peptide chain, in which the N-terminal has a protecting group. That is, Fmoc can be deprotected with $NH_3$, aminoethanol, dimethylamine, diethylamine, piperidine, piperazine or DBU; Boc or Tr can be deprotected with hydrochloric acid, sulfuric acid, phosphoric acid, acetic acid, formic acid, trifluoroacetic acid, methylsulfonic acid, benzene sulfonic acid, p-toluene sulfonic acid or gaseous hydrogen chloride.

The second process for preparing a compound represented by formula (I) disclosed in the present invention:

A compound represented by formula (I) is obtained by reacting a compound represented by formula (VI) in which $R^{20}$ represents OH with $R^8NCO$, wherein $R^8$ represents $C_{1-6}$ hydrocarbyl. The feed ratio of a compound represented by formula (VI) to $R^8NCO$ is 1:0.5 to 1:5. More suitable feed ratio of a compound represented by formula (VI) to $R^8NCO$ is 1:0.7 to 1:2. The optimal feed ratio of a compound represented by formula (VI) to $R^8NCO$ is 1:0.8 to 1:1.5.

Tertiary amine such as trimethylamine, triethylamine, pyridine, diisopropylethylamine, N-methylmorpholine, N-methyl piperidine, N-ethyl piperidine, 4-dimethylamino pyridine, 4-diethylamino pyridine, 4-(pyrrolidin-1-yl)pyridine or a mixture thereof can be added in the reaction. The adding molar amount of the tertiary amine is 0.5 to 10 folds of a compound represented by formula (VI). More suitable adding molar amount of the tertiary amine is 0.5 to 7 folds of a compound represented by formula (VI). The optimal adding molar amount of the tertiary amine is 0.5 to 3 folds of a compound represented by formula (VI). 4-dimethylamino pyridine, 4-diethylamino pyridine, 4-(pyrrolidin-1-yl)pyridine or a mixture thereof can be optionally added as a catalyst in the reaction. The adding molar amount of the catalyst is 0.01 to 1 fold of a compound represented by formula (VI). More suitable adding molar amount of the catalyst is 0.02 to 0.8 folds of a compound represented by formula (VI). The optimal adding molar amount of the catalyst is 0.05 to 0.3 folds of a compound represented by formula (VI). The reaction temperature is −10 to 120° C. More suitable temperature is 0 to 100° C. The most suitable reaction temperature is 20 to 100° C. The reaction is carried out in a solvent such as dichloromethane, chloroform, ethyl acetate, methyl acetate, ethyl propionate, methyl propionate, acetone, tetrahydrofuran, ethylene glycol dimethyl ether, ethylene glycol diethyl ether, N,N-dimethylformamide, N,N-diethylformamide, dimethyl sulfoxide, acetonitrile or a mixture thereof.

The third process for preparing a compound represented by formula (I) disclosed in the present invention:

A compound represented by formula (VI) in which $R^{20}$ represents OH can react with phosgene, diphosgene or triphosgene, and then $HNR^8R^9$ is added to obtain a compound represented by formula (I). The feed ratio by mole of a compound represented by formula (VI) to phosgene, diphosgene or triphosgene is 1:0.5 to 1:5. More suitable feed ratio by mole of a compound represented by formula (VI) to phosgene, diphosgene or triphosgene is 1:0.7 to 1:3. The optimal feed ratio by mole of a compound represented by formula (VI) to phosgene, diphosgene or triphosgene is 1:0.9 to 1:2. The feed ratio by mole of a compound represented by formula (VI) to $HNR^8R^9$ is 1:0.5 to 1:5. More suitable feed ratio by mole of a compound represented by formula (VI) to $HNR^8R^9$ is 1:0.7 to 1:3. The optimal feed ratio by mole of a compound represented by formula (VI) to $HNR^8R^9$ is 1:0.9 to 1:2.

An acid binding agent such as potassium carbonate, sodium carbonate, potassium bicarbonate, sodium bicarbonate, cesium carbonate, tertiary amine such as trimethylamine, triethylamine, pyridine, diisopropylethylamine, N-methylmorpholine, N-methyl piperidine, N-ethyl piperidine, 4-dimethylamino pyridine, 4-diethylamino pyridine, 4-(pyrrolidin-1-yl)pyridine or a mixture thereof can be added in the reaction. The adding molar amount of the acid binding agent is 1 to 20 folds of a compound represented by formula (VI). More suitable adding molar amount of the acid binding agent is 1.5 to 15 folds of a compound represented by formula (VI).

The optimal adding molar amount of the acid binding agent is 2 to 10 folds of a compound represented by formula (VI). 4-dimethylamino pyridine, 4-diethylamino pyridine, 4-(pyrrolidin-1-yl)pyridine or a mixture thereof can be optionally added as a catalyst in the reaction. The adding molar amount of the catalyst is 0.01 to 1 fold of a compound represented by formula (VI). More suitable adding molar amount of the catalyst is 0.02 to 0.8 folds of a compound represented by formula (VI). The optimal adding molar amount of the catalyst is 0.05 to 0.3 folds of a compound represented by formula (VI). The reaction temperature is −100 to 120° C. More suitable temperature is −78 to 100° C. The most suitable reaction temperature is −78 to 80° C. The reaction is carried out in a solvent such as dichloromethane, chloroform, ethyl acetate, methyl acetate, ethyl propionate, methyl propionate, acetone, tetrahydrofuran, ethylene glycol dimethyl ether, ethylene glycol diethyl ether, N,N-dimethylformamide, N,N-diethylformamide, dimethyl sulfoxide, acetonitrile or a mixture thereof.

A compound represented by formula (I) can be used to prepare a medicament for treating cancer or tumor. The cancer includes, but is not limited to, intestine cancer, liver cancer, gastric cancer, breast cancer, lung cancer, renal cancer, cervical cancer, pancreatic cancer, ovarian cancer, prostatic cancer, cerebral glioma, lymphoma, skin cancer, melanoma, head and neck cancer, thyroid cancer, multiple bone marrow cancer and leukemia.

A medicament for treating cancer or tumor which is prepared from a compound represented by formula (I) can be used in combination with other suitable anticancer drugs, immunopotentiators, anticancer synergists, hormones or traditional Chinese medicine formulations, such as taxols anticancer drugs, camptothecins anticancer drugs, vinblastines anticancer drugs, cyclophosphamide, 5-fluorouracil, thalidomide, cisplatin, Revlimid, tarceva, Irresa, Gleveec and a mixture thereof. Where used in combination with another therapeutic agent, the medicament may be simultaneously or sequentially administrated.

A dosage form of a medicament for treating cancer or tumor which is prepared from a compound represented by formula (I) depends on the administration route, such as gastrointestinal administration, intravenous drip, intraperitoneal administration, intradermal administration, intramuscular administration, intranasal administration or local administration. The dosage form comprising at least one compound represented by formula (I) further comprises a suitable carrier, filler, solvent, diluent, colorant and/or adhesive, which are necessary for preparing the dosage form.

A dosage form of a medicament for treating cancer or tumor which is prepared from a compound represented by formula (I) is preferably a form of injection, which includes, but is not limited to, powder injection, freeze-dried powder injection, hydro-injection, emulsion and suspension.

Abbreviations: Su: succinimido; Bt: benzotriazol-1-yl; At: 7-azabenzotriazol-1-yl; Fmoc: (9H-Fluoren-9-ylmethoxy) carbonyl; Boc: tert-butoxycarbonyl; CBZ: benzyloxycarbonyl; Tr: trimethylphenyl; Alloc: allyloxycarbonyl; DBU: 1,8-Diazabicyclo[5.4.0]undec-7-ene.

SPECIFIC EMBODIMENTS

Example 1

3'-pyrrolyldoxorubicin

To a 1 L three-neck flask were added 3.076 g of doxorubicin hydrochloride, 300 ml of distilled water, 300 ml of 1,2-dichloroethane, 30 ml of 2,5-dimethoxytetrahydrofuran and 6 ml of glacial acetic acid. The mixture was heated under reflux under argon atmosphere. After the reaction was complete, the reaction solution was cooled to the room temperature. The reaction solution was poured into 200 ml of ice water. The mixture was placed to separate. The organic phase was washed once with 200 ml of saturated sodium chloride solution and dried over anhydrous magnesium sulfate, filtered and rotary-evaporated. Under stirring in an ice bath, 100 ml of 5% sodium bicarbonate aqueous solution was added into the aqueous phase. The mixture was extracted with chloroform (50 ml×3) and the chloroform layers were combined. The combined chloroform layer was washed once with 100 ml of saturated sodium chloride solution. The mixture was filtered and rotary-evaporated to remove the solvent. The resulting crude product was combined with the above crude product. The resultant product was purified by column chromatography and eluted with chloroform:methanol=35:1. 2.91 g of the product was obtained. MS: 592 (M−1).

Compounds in Examples 2 to 6 were prepared in the same manner as described in Example 1:

Example 2

3'-pyrrolyl-5-iminodaunomycin

MS: 576 (M−1).

Example 3

3'-pyrrolyl-idarubicin

MS: 547 (M−1).

Example 4

3'-pyrrolyl-esorubicin

MS: 577 (M−1).

Example 5

3'-pyrrolyldoxorubicin

MS: 577 (M−1).

Example 6

3'-pyrrolyl-4'-(pyran-2-yl)doxorubicin

MS: 677 (M−1).

Example 7

3'-succinimidodoxorubicin 100 mg of doxorubicin hydrochloride was added to a 50 ml single-neck round bottom bottle and dissolved with 3 ml of DMF. 63 µl of DIEA (diisopropyl ethyl amine) and 2 mg of DMAP (4-dimethylamino pyridine) were added and stirred for 10 min. 21 mg of succinic anhydride was added and stirred for 1 hour under argon atmosphere. The reaction liquid was rotary-evaporated. 20 ml of distilled water and 10 ml of chloroform were added to the resulting residue and the mixture was pumping filtered to obtain a filter cake. The filter cake was dried in vacuo. 18 mg of the filter cake was transferred into a 50 ml one-neck flask. To the one-neck flask, were added 5 ml of dichloromethane (dried with molecular sieves) and 12 μl of triethylamine (dried with molecular sieves), and then was added 69 mg of cyanuric chloride. The mixture was stirred at room temperature. 20 ml of dichloromethane was added to the reaction liquid. The mixture was washed once with 20 ml of water. The resulting organic phase was washed once with 20 ml of saturated sodium chloride solution. The solution was rotary-evaporated to remove the solvent. A crude product was obtained. The crude product was purified by thin-layer chromatography and developed with chloroform:methanol=22:1. The title compound was obtained. MS: 624 (M−1).

Compounds in Examples 8 to 11 were prepared in the same manner as described in Example 7:

Example 8

3'-glutarimidodoxorubicin

MS: 1296 (2M+H$_2$O)

Example 9

3'-maleimidodoxorubicin

MS: 623 (M).

Example 10

3'-(pyrido-(2,3)succinimido)doxorubicin

MS: 722 (M+EtOH).

Example 11

3'-(benzo-(2,3)succinimido)doxorubicin

MS: 1345 (2M).

Example 12

3'-butyrolactamdoxorubicin 10 mg of doxorubicin hydrochloride was dissolved in 5 ml of DMF (anhydrous). The temperature was lowered to 0 to 5° C. in an ice bath. 7 mg of diisopropylethylamine was added and stirred for 10 min. 2.4 mg of 4-chlorobutyryl chloride was added and the reaction was carried out for 30 min. 100 ml of water was added in an ice bath. The mixture was extracted three times with chloroform (50 ml×3) and the chloroform layers were combined. The mixture was washed once with saturated sodium chloride solution and dried over anhydrous magnesium sulfate, filtered and rotary-evaporated to remove the solvent. The crude product was purified by thin-layer chromatography and developed with chloroform:methanol=95:5. 8 mg of the product was obtained and the product was dissolved in 3 ml of DMF (anhydrous). Under argon atmosphere, the temperature was lowered to −5-0° C. in an ice bath. 0.3 mg of sodium hydride was added and the mixture was stirred for 24 hours. After the reaction was complete, 50 ml of water was added. The resultant mixture was extracted three times with chloroform (50 ml×3) and the chloroform layers were combined. The mixture was washed once with saturated sodium chloride solution, dried over anhydrous magnesium sulfate, filtered and rotary-evaporated to remove the solvent. The crude product was purified by thin-layer chromatography and developed with chloroform:methanol=30:1. 6 mg of the product was obtained. MS: 611.

Example 13

3'-pyrrolyldoxorubicin-14-oxo-hydrogen succinate 845 mg of 3'-pyrrolyldoxorubicin was added to a 50 ml single-neck flask and dissolved with 20 ml of chloroform. The temperature was lowered to −10° C. under argon atmosphere. 704 mg of DMAP and 570 mg of succinic anhydride were added. The mixture was stirred overnight. After the reaction was complete, 300 ml of chloroform was added to the reaction solution. The mixture was washed once with 100 ml of 5% citric acid aqueous solution, washed once with 100 ml of saturated sodium chloride solution, dried over anhydrous magnesium sulfate, filtered and rotary-evaporated. A crude product was obtained. The crude product was purified by column chromatography and eluted with chloroform:methanol:glacial acetic acid=475:25:5. 238 mg of the product was obtained. MS: 692 (M−1).

Compounds in Examples 14 to 25 were prepared in the same manner as described in Example 13:

Example 14

3'-pyrrolyl-esorubicin-14-oxo-hydrogen succinate

MS: 676 (M−1).

Example 15

3'-pyrrolyl-4'-(pyran-2-yl)doxorubicin-14-oxo-hydrogen succinate

MS: 776 (M−1).

Example 16

3'-succinimidodoxorubicin-14-oxo-hydrogen succinate

MS: 724 (M−1).

Example 17

3'-glutarimidodoxorubicin-14-oxo-hydrogen succinate

MS: 738 (M−1).

Example 18

3'-maleimidodoxorubicin-14-oxo-hydrogen succinate

MS: 722 (M−1).

Example 19

3'-(pyrido-(2,3)succinimido)doxorubicin-14-oxo-hydrogen succinate

MS: 773 (M−1).

Example 20

3'-(benzo-(2,3)succinimido)doxorubicin-14-oxo-hydrogen succinate

MS: 772 (M−1).

Example 21

3'-pyrrolyldoxorubicin-14,4'-oxo-hydrogen disuccinate

MS: 792 (M−1).

Example 22

3'-pyrrolyldoxorubicin-14-oxo-hydrogen maleate

MS: 690 (M−1).

Example 23

3'-pyrrolyldoxorubicin-14,4'-oxo-hydrogen dimaleate

MS: 788 (M−1).

Example 24

3'-pyrrolyldoxorubicin-14-oxo-hydrogen glutarate

MS: 730 (M+Na).

Example 25

3'-pyrrolyldoxorubicin-14,4'-oxo-hydrogen diglutarate

MS: 820 (M−1).

Example 26

3'-pyrrolyldoxorubicin-14-oxo-(3-nitro-2-carboxyl)benzoate 50 mg of 3'-pyrrolyldoxorubicin was added to a 50 ml single-neck flask and dissolved with 2.5 ml of chloroform. The temperature was lowered to −5° C. under argon atmosphere. 42 mg of DMAP and 65 mg of 3-nitrophthalic anhydride were added. The mixture was stirred overnight. After the reaction was complete, 150 ml of chloroform was added to the reaction solution. The mixture was washed once with 100 ml of 5% citric acid aqueous solution. The organic phase was washed once with 100 ml of saturated sodium chloride solution, dried over anhydrous magnesium sulfate, filtered and rotary-evaporated. After purifying by thin-layer chromatography and developed with chloroform:methanol:glacial acetic acid=450:50:5, the title product was obtained. MS: 785 (M−1).

Compounds in Examples 27 to 37 were prepared in the same manner as described in Example 26:

Example 27

3'-pyrrolyldoxorubicin-14-oxo-(3-fluoro-2-carboxyl)benzoate

MS: 758 (M−1).

Example 28

3'-pyrrolyldoxorubicin-14,4'-oxo-bis(3-fluoro-2-carboxyl)benzoate

MS: 925.

Example 29

3'-pyrrolyldoxorubicin-14-oxo-(2-carboxyl-6-fluoro)benzoate

MS: 758 (M−1).

Example 30

3'-pyrrolyldoxorubicin-14,4'-oxo-bis(6-fluoro-2-carboxyl)benzoate

MS: 925.

Example 31

3'-pyrrolyldoxorubicin-14-oxo-(3,4,5,6-tetrafluoro-2-carboxyl)benzoate

MS: 812 (M−1).

Example 32

3'-pyrrolyldoxorubicin-14,4'-oxo-bis(3,4,5,6-tetrafluoro-2-carboxyl)benzoate

MS: 1033 (M).

Example 33

3'-pyrrolyldoxorubicin-14-oxo-(2,4-dicarboxyl)benzoate

MS: 784 (M−1).

Example 34

3'-pyrrolyldoxorubicin-14,4'-oxo-bis(2,4-dicarboxyl)benzoate

MS: 978 (M).

Example 35

3'-pyrrolyldoxorubicin-14,4'-oxo-bis(2-carboxyl)benzoate

MS: 889 (M).

Example 36

3'-pyrrolyldoxorubicin-14-oxo-(3-carboxyl)pyridine-2-formate

MS: 741

Example 37

3'-pyrrolyldoxorubicin-14,4'-oxo-(3-nitro-2-carboxyl)dibenzoate

MS:

Example 38

3'-pyrrolyldoxorubicin-14-oxo-alaninate hydrochloride 59.3 mg of 3'-pyrrolyldoxorubicin and 10 ml of dichloromethane (dried with molecular sieves) were added to a 50 ml single-neck flask and stirred under argon atmosphere. 63 mg of Boc-alanine, 38 mg of EDC HCl and 12 mg of DMAP were added. After the reaction was complete, 50 ml of dichloromethane was added. The mixture was washed once with 100 ml of water. The aqueous layer was back-extracted with dichloromethane once and combined with the organic phase. The resulting phase was washed with 100 ml of saturated sodium chloride solution once, dried over anhydrous magnesium sulfate, filtered and rotary-evaporated. After purifying by thin-layer chromatography and developed with chloroform:methanol=35:1. 43 mg of the product was obtained. The resulting compound was dissolved with 1 ml of tetrahydrofuran (re-evaporated) and argon gas was introduced. The temperature was lowered to −5° C. 1 ml of solution of hydrogen chloride in diethyl ether was added. The mixture was stirred for 2 hours and then filtered. The filter cake was eluted three times with diethyl ether to obtain the title compound. MS: 665 (M+1).

Compounds in Examples 39 to 53 were prepared in the same manner as described in Example 38:

Example 39

3'-pyrrolyldoxorubicin-14-oxo-valinate hydrochloride

MS: 693 (M+1).

Example 40

3'-pyrrolyldoxorubicin-14-oxo-glycinate hydrochloride

MS: 651 (M+1).

Example 41

3'-pyrrolyldoxorubicin-14-oxo-leucinate hydrochloride

MS: 707 (M+1).

Example 42

3'-pyrrolyldoxorubicin-14-oxo-(2,2-dimethyl)glycinate hydrochloride

MS: 679 (M+1).

Example 43

3'-pyrrolyldoxorubicin-14-oxo-(2-phenyl)glycinate hydrochloride

MS: 727 (M+1).

Example 44

3'-pyrrolyldoxorubicin-14-oxo-2-diethylaminoacetate

MS: 707 (M+1).

Example 45

3'-pyrrolyldoxorubicin-14-oxo-2-morpholinylacetate

MS: 720 (M+1).

Example 46

3'-pyrrolyldoxorubicin-14-oxo-(N-glycyl)valinate hydrochloride

MS: 750 (M+1).

Example 47

3'-pyrrolyl-esorubicin-14-oxo-glycinate hydrochloride

MS: 635 (M+1).

Example 48

3'-pyrrolyl-4'-(pyran-2-yl)doxorubicin-14-oxo-glycinate hydrochloride

MS: 735 (M+1).

Example 49

3'-succinimidodoxorubicin-14-oxo-glycinate hydrochloride

MS: 683 (M+1).

Example 50

3'-glutarimidodoxorubicin-14-oxo-glycinate hydrochloride

MS: 697 (M+1).

Example 51

3'-maleimidodoxorubicin-14-oxo-glycinate hydrochloride

MS: 681 (M+1).

Example 52

3'-(pyrido-(2,3)succinimido)doxorubicin-14-oxo-glycinate hydrochloride

MS: 732 (M+1).

Example 53

3'-(benzo-(2,3)succinimido)doxorubicin-14-oxo-glycinate hydrochloride

MS: 731 (M+1).

Example 54

3'-pyrrolyldoxorubicin-14-oxo-β-alaninate hydrochloride

MS: 697 (M+1).

Cytotoxicity Assay (MTS Assay)

I. Cell Strains and Reagents

MCF-7: human breast cancer cell strains;
HCT-8: human colon cancer cell strains;
HEPG-2: human liver cancer cell strains;
A549: human lung cancer cell strains;
LOVO: human colon cancer cell strains;
RPMI 1640 culture solution; MTT: blue tetrazolium; DMSO: dimethyl sulfoxide; 96-well cell culture plate;
Antitumor compound (prepared by Tianjin Hemay Biotech co. Ltd);
Positive control drug: doxorubicin (prepared by Zhejiang Hisun Pharmaceutical Co. Ltd.).

II. Determination of Cell Growth Inhibition Activity

1. Cell Culture and Drug Treatment:

Cells were seeded into RPMI 1640 cell culture solution containing 10% fetal bovine serum (100 ku/L of penicillin and 100 ku/L of streptomycin were supplemented). The culture dish was placed in a cell incubator containing 5% $CO_2$ at 37° C. The culture solution was changed once every 2-3 days. Cells were digested with 0.25% trypsin liquid, passaged and collected.

Cells during the logarithmic growth phase were formulated into a cell suspension having a desired concentration with RPMI 1640 cell culture solution containing 10% fetal bovine serum. The cell suspension was added onto 96 well cell culture plate at 3000-5000 per well (100 μl). After incubating for 24 hours, 100 μl of the test substances with different concentration was added per well. There were four parallel wells for each concentration in this plate. After incubating for 72 to 120 hours, the supernatant was discarded. To each well was added 100 μl of new formulated 0.5 mg/ml MTT serum-free culture solution. After incubating for 4 hours at 37° C., the supernatant was discarded. Formazane was dissolved with 200 μl DMSO. After slightly oscillating for 15 min, absorbance values (OD value) at the detective wavelength of 570 nm and the reference wavelength of 450 nm were determined with enzyme labeling instrument.

2. Data Processing

Data was represented by x±s. The inhibition rate=(OD value of the control group−OD value of the administration group)/OD value of the control group×100%. The maximum inhibition rate $I_{max}$ and the half effective concentration ($IC_{50}$) represent the anticancer effects. Figures were drawn with MicroCal Origin software. The inhibition curve of the test substance to the growth of tumor cells was fitted by Four Parameters Logistic Program of the software. The half effective concentration ($IC_{50}$: μg/ml) for inhibiting the proliferation of tumor cells was calculated.

3. Results

The exposure concentrations of the test substance were 0.001 μg/ml, 0.003 μg/ml, 0.009 μg/ml, 0.027 μg/ml, 0.082 μg/ml, 0.247 μg/ml, 0.741 μg/ml, 2.222 μg/ml, 6.667 μg/ml and 20 μg/ml. The exposure concentrations of doxorubicin (positive drug) were 1.25 μg/ml, 5 μg/ml, 20 μg/ml. In a 96-well plate, 3000-5000 cells were inoculated in each well and there were four parallel wells for each concentration. Table 1 lists the growth inhibition rate of the compounds against Lovo cells at concentration of 1 μM. Table 2 lists the inhibition activity of the compounds against various tumor cells. Table 3 lists the inhibition rate of the compounds against the hyperplasia of MCF-7 human breast cancer cells at various concentrations.

TABLE 1

Growth Inhibition Rate of Compounds against Lovo Cells at Concentration of 1 μM

| Compounds | Growth Inhibition Rate (%) |
| --- | --- |
| Doxorubicin | 50.35 |
| Example 1 | 80.62 |
| Example 2 | 74.0 |
| Example 3 | 88.9 |
| Example 4 | 40.71 |
| Example 5 | 67.25 |
| Example 6 | 90.94 |
| Example 7 | 83.31 |
| Example 13 | 76.05 |
| Example 38 | 78.44 |

TABLE 2

Inhibition Activity of Compounds against Tumor Cells

| | Half-Inhibitory Concentration of Cells Growth ($EC_{50}$) (μM) | | | |
| --- | --- | --- | --- | --- |
| Compounds | MCF-7 cell | HCT-8 cell | HEPG-2 | A549 cell |
| Doxorubicin | 1.2 | 0.9 | 2.0 | 0.66 |
| Example 1 | 0.21 | 0.49 | 0.81 | 0.061 |
| Example 13 | 0.93 | 1.87 | 0.15 | 2.36 |
| Example 38 | 0.87 | 0.59 | 1.06 | 0.23 |

TABLE 3

Inhibition Effects of Compound in Example 1 on Hyperplasia of MCF-7 Human Breast Cancer Cells

| Compound Concentration (μg/ml) | A570 nm-OD Values | Inhibition Rate (%) | Main Parameters |
|---|---|---|---|
| 0 | 1.701 ± 0.161 | | $IC_{50} =$ |
| 0.001 | 1.629 ± 0.257 | 4.27 | 0.06023 ± 0.01528 μg/ml |
| 0.003 | 1.744 ± 0.176 | −2.49 | $I_{max} = 83.03\%$ |
| 0.009 | 1.443 ± 0.079 | 15.17 | |
| 0.027 | 1.238 ± 0.072 | 27.22 | |
| 0.082 | 0.883 ± 0.041 | 48.09 | |
| 0.247 | 0.703 ± 0.058 | 58.68 | |
| 0.741 | 0.461 ± 0.026 | 72.89 | |
| 2.222 | 0.302 ± 0.030 | 82.26 | |
| 6.667 | 0.320 ± 0.030 | 81.18 | |
| 20 | 0.289 ± 0.019 | 83.03 | |

The activity of the test compounds is equivalent to or slightly better than the activity of doxorubicin. Moreover, the test compounds have better growth inhibition effects on various human tumor cell strains, such as human colon cancer LOVO cell strains, human breast cancer MCF-7 cell strains, colon cancer HCT-8 cell strains, liver cancer HEPG-2 cell strains and lung cancer A549 cell strains.

Example 1

In Vivo MTD Test Report in Mice

Experiment purpose: preliminary investigation on in vivo toxicity of the compound in Example 1 in mice
Experiment animal: Kunming white mice 20±2 g, purchased from the animal housing in Institute of Radiation Medicine, Chinese Academy of Medical Sciences. Animal license No.: SCXK(JIN)2005-0001.
Experiment Drug: Compound in Example 1
Preparation of drug solution: After the drug was vortexed to dissolve with 0.5% (V/V) of DMSO, 5% (V/V) of RH40 (ethoxylated hydrogenated castor oil) was added. After mixing with vortex, the volume was determined with normal saline.
Experiment Scheme:
(1) Single administration: Nine healthy Kunming male white mice, of which the body weights are 20±2 g, were divided into three groups: 2 mice belong to the control group; 6 mice belong to 20 mg/kg group; 1 mouse belongs to 30 mg/kg group. 20 mg/kg and 30 mg/kg of the compound in Example 1 were administrated once via tail vein injection to the mice in the administration group. The same volume of a solvent was administrated as control to the mice in the control group. After administration, conditions such as action, reflex, locomotor activity and the like of the mice were observed within one hour. Subsequently, the body weights of the mice were recorded every day. Having observed for 14 days after drug withdrawal, the mice were anatomized to observe whether their main organs have an obvious abnormality.
(2) Multiple administrations: Twelve healthy Kunming white mice including six male mice and six female mice, of which the body weights are 20±2 g, were divided into two groups: 1 mouse belongs to the control group; 5 mice belong to 10 mg/kg group. 10 mg/kg of the test drug was administrated once every three days via tail vein injection to the mice in the administration group. The same volume of a solvent was administrated as the control to the mice in the control group. The mice in each group were administrated five times. After each administration, conditions such as action, reflex, locomotor activity and the like of the mice were observed within one hour. The body weights of mice were recorded every day. Having been fed normally for one week after drug withdrawal, the mice were anatomized to observe whether their main organs have an obvious abnormality.

Experiment Results:

1. Mortality Rate:
  (1) Single administration: Death was not found.
  (2) Multiple administrations: Death was not found.
2. Change of Body Weight:
  (1) Single administration: The body weight of each mouse increased after administration, and no obvious abnormality on the body surface was observed.
  (2) Multiple administrations: The body weight of each mouse increased slowly after administration, and no obvious abnormality on the body surface was observed.

CONCLUSION

The maximal tolerance dose (MTD) of the test compound is at least more than five folds higher than that of doxorubicin (MTD: 8-12 mg/kg).

The invention claimed is:
1. A compound represented by formula (I), or a salt thereof:

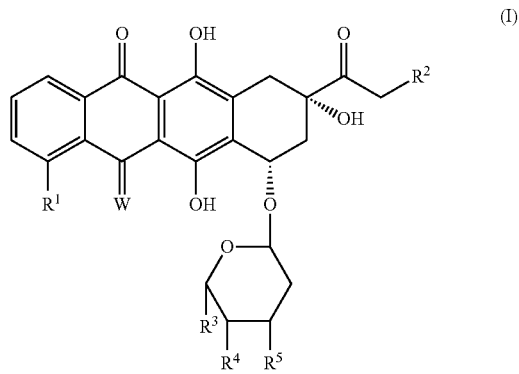

wherein $R^1$ represents H, $C_{1-4}$ hydrocarbyl or $OC_{1-4}$ hydrocarbyl;

$R^2$ represents H or $OR^6$, wherein, $R^6$ is selected from the group consisting of H, $C(O)R^8$, a peptide chain, $C(O)NH_2$, $C(O)NR^8R^9$, $C(O)Ar$—$R^{27}$, $C(O)(C_{2-4}$ hydrocarbylidene) COOH and a group represented by formula (II); $R^8$ and $R^9$ each independently represent H or $C_{1-6}$ hydrocarbyl, or $NR^8R^9$ represents pyrrolidin-1-yl, piperidin-1-yl or morpholin-1-yl; Ar represents an aromatic ring or an aromatic heterocyclic ring; $R^{27}$ represents 0 to 5 identical or different groups selected from the group consisting of F, Cl, $NO_2$, CN, OH, SH, COOH, $NH_2$, $NR^8R^9$, $C_{1-6}$ hydrocarbyl, $OC_{1-6}$ hydrocarbyl, $OC(O)C_{1-6}$ hydrocarbyl, $C(O)OC_{1-6}$ hydrocarbyl, $SC_{1-6}$ hydrocarbyl, $S(O)C_{1-6}$ hydrocarbyl and $S(O)_2C_{1-6}$ hydrocarbyl; a peptide chain represents a single natural amino acid, a single unnatural amino acid or peptide chain consisting of 2 to 4 natural amino acids and/or unnatural amino acids;

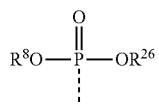

(II)

$R^{26}$ represents H or $C_{1-6}$ hydrocarbyl;
W represents O or NH;
$R^3$ represents H, F, $OC_{1-4}$ hydrocarbyl or $C_{1-4}$ hydrocarbyl;
$R^4$ represents H, F, $C_{1-4}$ hydrocarbyl or $OR^7$, wherein $R^7$ represents H, 2-pyranyl or $R^6$;
$R^5$ is represented by formula (V);

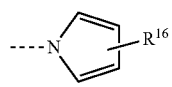

(V)

wherein
$R^{16}$ is selected from the group consisting of H, F, Cl, CN, $NO_2$, $NH_2$, OH, $C(O)OC_{1-4}$ hydrocarbyl, $OC(O)C_{1-4}$ hydrocarbyl, $OC_{1-4}$ hydrocarbyl, $C_{1-4}$ hydrocarbyl, $SC_{1-6}$ hydrocarbyl, $S(O)C_{1-6}$ hydrocarbyl, $S(O)_2C_{1-6}$ hydrocarbyl, $(C_{0-4}$ hydrocarbylidene)Ar—$R^{27}$ and $NR^8R^9$.

2. The compound of claim 1, wherein $R^1$ represents H, OH or $OCH_3$.

3. The compound of claim 1, wherein W represents O.

4. The compound of claim 1, wherein $R^2$ is selected from the group consisting of H, OH, hydrogen succinate group, hydrogen glutarate group, hydrogen maleate group, (3-nitro-2-carboxyl)benzoate group, (3-fluoro-2-carboxyl)benzoate group, (2-carboxyl-6-fluoro)benzoate group, (3,4,5,6-tetrafluoro-2-carboxyl)benzoate group, (2,4-dicarboxyl)benzoate group, (2-carboxyl)benzoate group, (3-carboxyl)pyridine-2-formate group, alaninate group, valinate group, glycinate group, leucinate group, (2,2-dimethyl)glycinate group, (2-phenyl)glycinate group, 2-diethylaminoacetate group, 2-morpholinylacetate group and (N-glycyl) valinate group.

5. The compound of claim 1, wherein $R^3$ represents H or $CH_3$.

6. The compound of claim 1, wherein $R^4$ is selected from the group consisting of H, F, OH, $OCH_3$, 2-pyranyl, hydrogen succinate group, (3-nitro-2-carboxyl)benzoate group, (2-carboxyl)benzoate group, (2,4-dicarboxyl)benzoate group, (3,4,5,6-tetrafluoro-2-carboxyl)benzoate group, (2-carboxyl-6-fluoro)benzoate group and (3-fluoro-2-carboxyl)benzoate group.

7. The compound of claim 1, wherein $R^5$ is pyrrol-1-yl.

8. The compound of claim 1, wherein the compound is selected from the group consisting of:
3'-pyrrolyl-5-iminodaunomycin,
3'-pyrrolyl-idarubicin,
3'-pyrrolyl-esorubicin,
3'-pyrrolyldoxorubicin, and
3'-pyrrolyl-4'-(pyran-2-yl)doxorubicin.

9. A compound selected from the group consisting of:
3'-pyrrolyl-esorubicin-14-hydrogen succinate,
3'-pyrrolyl-4'-(pyran-2-yl)doxorubicin-14-hydrogen succinate,
3'-pyrrolyldoxorubicin-14,4'-hydrogen disuccinate,
3'-pyrrolyldoxorubicin-14-hydrogen maleate,
3'-pyrrolyldoxorubicin-14,4'-hydrogen dimaleate,
3'-pyrrolyldoxorubicin-14-hydrogen glutarate,
3'-pyrrolyldoxorubicin-14,4'-hydrogen diglutarate,
3'-pyrrolyldoxorubicin-14-(3-nitro-2-carboxyl)benzoate,
3'-pyrrolyldoxorubicin-14-(3-fluoro-2-carboxyl)benzoate,
3'-pyrrolyldoxorubicin-14,4'-bis(3-fluoro-2-carboxyl)benzoate,
3'-pyrrolyldoxorubicin-14-(2-carboxyl-6-fluoro)benzoate,
3'-pyrrolyldoxorubicin-14,4'-bis(6-fluoro-2-carboxyl)benzoate,
3'-pyrrolyldoxorubicin-14-(3,4,5,6-tetrafluoro-2-carboxyl)benzoate,
3'-pyrrolyldoxorubicin-14,4'-bis(3,4,5,6-tetrafluoro-2-carboxyl)benzoate,
3'-pyrrolyldoxorubicin-14-(2,4-dicarboxyl)benzoate,
3'-pyrrolyldoxorubicin-14,4'-bis(2,4-dicarboxyl)benzoate,
3'-pyrrolyldoxorubicin-14,4'-bis(2-carboxyl)benzoate,
3'-pyrrolyldoxorubicin-14-(3-carboxyl)pyridine-2-formate,
3'-pyrrolyldoxorubicin-14,4'-(3-nitro-2-carboxyl)dibenzoate,
3'-pyrrolyldoxorubicin-14-alaninate hydrochloride,
3'-pyrrolyldoxorubicin-14-valinate hydrochloride,
3'-pyrrolyldoxorubicin-14-glycinate hydrochloride,
3'-pyrrolyldoxorubicin-14-leucinate hydrochloride,
3'-pyrrolyldoxorubicin-14-(2,2-dimethyl)glycinate hydrochloride,
3'-pyrrolyldoxorubicin-14-(2-phenyl)glycinate hydrochloride,
3'-pyrrolyldoxorubicin-14-2-diethylaminoacetate,
3'-pyrrolyldoxorubicin-14-2-morpholinylacetate,
3'-pyrrolyldoxorubicin-14-(N-glycyl)valinate hydrochloride,
3'-pyrrolyl-esorubicin-14-glycinate hydrochloride,
3'-pyrrolyl-4'-(pyran-2-yl)doxorubicin-14-glycinate hydrochloride, and
3'-pyrrolyldoxorubicin-14-β-alaninate hydrochloride.

10. A method for treating an abnormal cell proliferation disease in a subject, comprising administering to the subject a therapeutically effective amount of the compound of claim 1, wherein the disease is selected from the group consisting of liver cancer, breast cancer, colon cancer, non-small cell lung cancer, and melanoma.

11. A method of claim 10, wherein the administering comprises injecting.

12. A method of claim 11, wherein the injecting comprises injecting an aqueous solution, emulsion, or a suspension.

* * * * *